United States Patent [19]

Smith

[11] 4,007,153

[45] Feb. 8, 1977

[54] SILICONE DENTAL IMPRESSION COMPOSITIONS

[75] Inventor: Robert A. Smith, Schnectady, N.Y.

[73] Assignee: General Electric Company, Waterford, N.Y.

[22] Filed: June 19, 1975

[21] Appl. No.: 588,202

[52] U.S. Cl. .................... 260/33.6 SB; 260/37 SB
[51] Int. Cl.$^2$ ........................................ C08K 5/01
[58] Field of Search ............... 260/37 SB, 33.6 SB, 260/18 SB

[56] References Cited

UNITED STATES PATENTS

| | | | |
|---|---|---|---|
| 3,127,363 | 3/1964 | Nitzsche et al. | 260/18 S |
| 3,607,801 | 9/1971 | Fulton | 260/37 SB X |
| 3,696,090 | 10/1972 | Lampe | 260/18 S |

Primary Examiner—Lewis T. Jacobs
Attorney, Agent, or Firm—John L. Young; E. Philip Koltos; Edward A. Hedman

[57] ABSTRACT

Two-part room-temperature vulcanizing silicone dental impression compositions are provided which, before curing, consist essentially of a metallic salt of a monocarboxylic acid as a catalyst and a base compound. In one embodiment the base compound consists of a fluid diorganopolysiloxane, an organosilicon cross-linker and a unique filler combination of an admixture of zinc oxide, calcium carbonate and pumice. In another embodiment, the base compound consists of a fluid diorganopolysiloxane, an organosilicon cross-linker, mineral oil and a low oil absorption calcium carbonate filler.

17 Claims, No Drawings

SILICONE DENTAL IMPRESSION COMPOSITIONS

The present invention relates to improved silicone compositions for making detailed impressions of the mouth, gums and teeth. More particularly, it concerns two-part room-temperature-vulcanizing silicone compositions, one part being a metallic salt of a monocarboxylic acid as a catalyst and the second part being the base compound. In one embodiment the base compound consists of a diorganopolysiloxane, an organosilicon for cross-linking and a new improved filler, which is an admixture of zinc oxide, calcium carbonate and pumice. In a second embodiment, the base compound consists of a diorganopolysiloxane, an organosilicon cross-linker, mineral oil and, as an improved filler, a low oil absorption calcium carbonate.

BACKGROUND OF THE INVENTION

Room temperature-vulcanizing silicone rubber has enjoyed increasingly wider use in dentistry as a molding medium in the preparation of artificial dentures. The material is used as a paste into which a curing agent is mixed before use. It then changes from a pasty consistency to a rubber-elastic state upon curing at body temperature. Because of its elasticity, the cured silicone can be removed from the mouth easily and can then be used for casting a working model, such as with plaster of paris, from which the permanent dental piece is made.

Silicone rubber compositions offer several advantages over materials formerly used as a dental replica material, e.g., plaster, alginate, etc. As compared with plaster, silicone rubber is more elastic, has better resistance to breakage and offers good release from the jaw. As compared with alginates, silicone rubber is not sensitive to loss of water (which may cause shrinkage) and possesses better molding accuracy. Silicones also provide good dimensional stability which is retained even on prolonged storage in the air (For reference, see "Chemistry and Technology of Silicones", Walter Noll, Academic Press, New York, 1968, p. 623.)

Elastomeric compositions have been utilized in two main areas of dental impression work — one, crown and bridge work and, two, preparation of full dentures. Crown and bridge work requires a custom tray which is usually prepared by first making an impression with alginate of the area of the mouth to be repaired. A cast of this impression is then made by pouring dental stone into the hardened alginate and curing it. The cast is then wrapped with asbestos and a form is built up around the wrapped casting using methyl methacrylate or some other suitable polymeric material (e.g., polyethylene, polyvinyl chloride, polyepoxide, etc.). After the methyl methacrylate has been cured, it is removed from around the dental stone casting and used as the custom tray for the silicone rubber impression that will be made.

The methyl methacrylate custom tray is first coated with a primer. Then a silicone of pasty consistency is mixed with a curing agent and some suitable catalyst, placed into the tray, and the tray is inserted into the patient's mouth where curing takes place. After this initial impression has cured, it is removed and trimmed to eliminate undercuts and thin-walled sections. Then a silicone compound of lower viscosity is catalyzed and inserted into the patient's mouth directly over the area to be repaired. The custom tray containing the cured silicone rubber initial impression is pressed firmly into place over the catalyzed silicone until curing is complete. This part of the procedure is then finished, and the now highly detailed impression of the patient's mouth is forwarded to a laboratory for the making of a bridge.

For the preparation of full dentures, the silicones are utilized in much the same manner, except that a re-usable metal perforated tray is used instead of a custom tray made of polymeric materials. The high viscosity silicone compound is placed into the tray as before, inserted into the mouth to make a first impression, and this is followed by the use of a lower viscosity silicone compound to make a more detailed impression of the area of the mouth to be repaired, substantially as described above.

An elastic silicone composition which can be used to obtain room temperature vulcanizing dental impressions as described above is disclosed in Nitzsche et al, U.S. Pat. No. 3,127,363, the disclosure of which is incorporated herein by reference. Nitzsche et al disclose organopolysiloxane elastomeric compositions that are vulcanizable at room temperature and are taught as being useful for a variety of purposes, including the making of casts of the mouth and teeth. However, these compositions are not specifically adapted to some of the requirements relating uniquely to the making of dental impressions.

Lampe, U.S. Pat. No. 3,696,090, incorporated herein by reference, discloses a room temperature curable silicone rubber composition which can be used making ear plugs. However, relatively small amounts of filler (10–50%) must be employed or the composition is difficult to mold.

There have now been discovered new improved two-part silicone rubber compositions which are vulcanized at room temperature and are adapted for making dental impressions. The present compositions provide desired properties such as moderately fast "pot life", putty-like consistency, good shelf stability, low linear shrinkage, and low-toxicity. Vulcanization of the compositions of the present invention is not inhibited by materials from which the custom trays are made, e.g., polyacrylics, polyethylene, polyvinylchlorides, epoxies, and the like.

The compositions achieve greater hardness (durometer build-up) within a shorter time after cure, and can be formulated to cure to a smooth, non-grainy appearance.

In addition, the need for custom tray fabrication by the dentist is eliminated because the compositions of the present invention can be employed both as the custom tray material and as the high viscosity compound which is inserted into the tray to make dental impressions. Moreover, bite registration, which usually requires a separate operation with either a custom tray made of methyl methacrylate or the like or a metal perforated tray, can now be obtained with the present silicone putty tray material at the same time as the dental impression.

The detailed compositions are not disclosed in the prior art, and the remarkable properties, as dental impression materials, are not obvious from anything disclosed or remotely suggested in the prior art.

DESCRIPTION OF THE INVENTION

According to the present invention there are provided two-part room temperature vulcanizing silicone compositions for taking dental impressions. The first embodiment can be formulated to be high flow and tacky, or a low flow and non-tacky, dental impression composition using a unique filler combination. Before curing, this composition consists essentially of from about 0.3 to about 0.7 parts by weight of a metallic salt of a monocarboxylic acid to 100 parts of a base compound consisting essentially of:

a. from about 25 to about 35% by weight of a fluid diorganopolysiloxane containing terminal silicon-bonded hydroxy groups;

b. from about 60 to about 75% by weight of a filler composition consisting essentially of an admixture of zinc oxide, calcium carbonate and pumice; and c. from about 0.05 to about 2% by weight of an organo-silicon cross-linker having the general formula

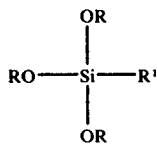

wherein R is a radical selected from the group consisting of alkyl, alkenyl and aryl radicals and $R^1$ is a radical selected from the group consisting of alkyl, alkenyl, aryl and alkoxy radicals.

The composition consists of two parts, a base compound and catalyst. The base compound consists of a silicone fluid, a filler and an organo-silicon cross-linker. An effective amount of catalyst is worked into the base compound to catalyze it prior to making the dental impression. It is desirable, of course, to obtain a composition which has the consistency of putty for easier workability. The specified formulation has a putty-like consistency.

The preferred silicone fluid for the base compound is a silanol-stopped dimethylpolysiloxane (i.e., having terminal silicon bonded hydroxy groups) with a viscosity of from 3,000 to 200,000 cps. at 25° C., and especially preferably a viscosity of from 3,000 to 120,000 cps. at 25° C. When polysiloxanes of 80,000 to 120,000 cps. are used, a low molecular weight silanol stopped polydimethylsiloxane containing 5 to 10 dimethyl disiloxane units and about 7% by weight of hydroxyl groups is employed in small but effective amounts to slow curing time. An especially effective amount of this low molecular weight silicone is from 0.05 to 2% by weight of the total base compound.

When a polyorganosiloxane of a lower viscosity value is employed, e.g., 2,500 to 3,500 cps. at 25° C., the base compound has high flow and is tacky to the touch prior to catalyzing and non-tacky after catalyzing. When a polyorganosiloxane of a relatively higher viscosity is used, e.g., 80,000 to 120,000 cps. at 25° C., the base compound has low flow and is non-tacky to the touch prior to catalyzing.

The amount of catalyst employed with the base compound will vary depending upon the viscosity of the latter. When diorganopolysiloxanes having a viscosity of from 80,000 to 120,000 cps. at 25° C. are employed in the base compound, a weight ratio of about 0.6 parts of catalyst to 100 parts of the base compound is preferred. With polysiloxanes of much lower viscosity, e.g., 2,500 to 3,500 cps., a lower amount of catalyst is used, such as about 0.4 parts of catalyst to 100 parts of the base compound.

The unique filler which is incorporated into the silicone fluid consists of an admixture of 3 to 15 parts, preferably 5 to 10, of zinc oxide, 5 to 25 parts, preferably 10 to 20, of calcium carbonate and 45 to 65 parts, preferably 50 to 60, of pumice ($Al_2O_3$-$SiO_2$), based on 100 parts by weight of the base. The various components of the filler work in combination. Calcium carbonate and zinc oxide are used as bulking as well as whitening agents. Pumice is used to provide a putty-like consistency to the composition. Pumice is also more easily wetted into the formulation and thus assures more consistency from batch to batch than other types of filler. Surprisingly, it has also been found that when pumice is used as a component of the filler, greater hardness is obtained with the composition within a relatively short time after addition of the catalyst and curing. All three components of the filler must be present to produce the advantageous results achieved with this embodiment.

The preferable cross-linking agents are conventional organosilicon compounds used for this purpose having the general formula

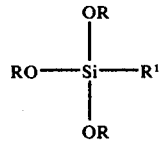

wherein R is a radical selected from the group consisting of alkyl, alkenyl and aryl radicals and $R^1$ is a radical selected from the group consisting of alkyl, alkenyl, aryl and alkoxy radicals.

Some preferred cross-linking agents are phenyl triethoxy silane, vinyl triethoxysilane, n-propyl silicate and condensed ethyl orthosilicate. Especially preferred is condensed ethyl orthosilicate.

Generally, from about 0.05 to about 2% by weight of the total base compound of the organo-silicon cross-linker is employed. Amounts less than this are generally insufficient to react with the organopolysiloxane to form the cured silicone rubber, and amounts larger than this tend to reduce the elasticity of the cured rubber.

Catalysts suitable for the present dental impression compositions are conventional and well known. Metal salts of monocarboxylic acids have been found to be effective. Various acid radicals and metal ions are suitable as components in the metal salts. Some preferred acid radicals are the linoleate, stearate, oleate, acetate, butyrate and octoate. Tin is especially preferred for the metal ion because of its low toxicity. Some preferred metal salts are tin oleate, tin butyrate and tin octoate. Especially preferred is tin octoate.

In a second embodiment there is provided a room temperature vulcanizing silicone dental impression composition which is non-sticky, or, at most, slightly tacky and which cures to a smooth high durometer composition which does not have a "grainy", "gritty", or coarse feel. This embodiment, before curing, consists essentially of from about 0.3 to about 0.7 parts by weight of a tin salt of a monocarboxylic acid to 100 parts of a base compound consisting essentially of:

a. from about 15 to about 25% by weight of a fluid diorganopolysiloxane containing terminal silicon-bonded hydroxy groups;

b. from about 70 to about 85% by weight of a filler consisting essentially of low oil absorption calcium carbonate;

c. from about 3 to about 8% by weight of mineral oil; and d. from about 0.05 to about 2% by weight of an organo-silicon cross-linker having the general formula

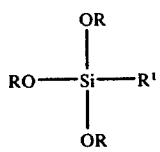

wherein R is a radical selected from the group consisting of alkyl, alkenyl and aryl radicals and $R^1$ is a member of the group consisting of alkyl, alkenyl, aryl and alkoxy groups, said composition having a non-sticky, or at most, a slight "tacky" feel before curing, and smooth, non-grainy feel after curing. Some embodiments have a slight gritty feel, which is not necessarily disadvantageous.

The diorganopolysiloxane of this embodiment is preferably a dimethylpolysiloxane having a viscosity of from 15,000 to 35,000 cps. at 25° C. and, especially preferably, a viscosity of from about 20,000 to about 30,000 cps. at 25° C.

Effective as cross-linking agents are the same organo-silicon compounds mentioned above as suitable for the compositions of the first embodiment.

A relatively small amount of mineral oil is added to reduce or eliminate any stickiness in the base compound and facilitate its handling during the making of dental impressions. Suitable mineral oils will be the physiologically-acceptable bland fluids available from a number of commercial sources. One suitable mineral oil is the heavy white oil known as Kaydol Mineral Oil available from Sonneborn Division of Witco Chemical Co.

For the catalyst, the same conventional metal salts of monocarboxylic acids mentioned above as suitable for the compositions of the first embodiment are also suitable for these compositions.

The filler is a low oil absorption calcium carbonate, which has been found to aid in providing a smooth, non-grainy appearance and feel to the cured silicone composition. Suitable grades of low oil absorption calcium carbonates and their suppliers, are Camel Kote (Harry T. Campbel and Sons Co., Towson, Md.), Gamma Sperse 255, Wingdale White and No. 10 White (Georgia Marble Company, Calcium Products Division, Tate, Ga.), Duramite (Thompson, Weinman and Company, Montclair, N.J.), and Micro White 75 (Sylacauga Calcium Products Co., Sylacauga, Al.). Especially preferred is Camel Kote calcium carbonate.

The present invention is illustrated by the examples given below, which are not intended to limit the scope of the invention.

EXAMPLES 1-2

These examples are illustrative of the preparation and properties of the compositions of the first embodiment referred to above. All proportions are on a percent by weight basis.

The base compound of Mixture A (Example 1) is prepared by thoroughly mixing 30.67 parts of silanol-stopped polydimethylsiloxane having a viscosity of about 3,000 cps. at 25° C., 12.26 parts of calcium carbonate reinforcing filler (Albacar), 6.15 parts of zinc oxide filler (XX-78) 50.02 parts of pumice filler (Airfloat 2599, commercially available from James H. Rhodes and Co., Long Island City, N.Y.) and 0.90 parts of condensed ethyl orthosilicate. The blend is worked until a putty consistency is obtained. This is high flow and tacky to the touch. Stannous octoate catalyst in the amount of about 0.4 parts per 100 parts of base compound is then worked into the putty to yield Mixture A, which cures at room temperature.

Mixture B (Example 2) is similarly prepared. The base compound of B is first obtained by mixing thoroughly 30.34 parts of silanol-stopped polydimethylsiloxane having a viscosity of about 120,000 cps. at 25° C., 12.16 parts of calcium carbonate filler (Albacar), 6.11 parts of zinc oxide filler (XX-78), 49.63 parts of pumice filler (Airfloat 2599), 0.89 parts of condensed ethyl orthosilicate and, to slow pot life, 0.78 parts of low molecular weight silanol-stopped polydimethylsiloxane having about 7% by weight of hydroxy groups. This composition is low flow and non-tacky to the touch. To the resulting putty is added about 0.6 parts of stannous octoate per 100 parts of base compound to obtain Mixture B, which cures at room temperature.

The properties of the compositions are summarized in Table 1

TABLE 1

| ROOM-TEMPERATURE VULCANIZING DENTAL IMPRESSION COMPOSITIONS | | |
|---|---|---|
| Example (Mixture) | 1(A) | 2(B) |
| Application Rate at 90 P.S.I. in gm./min. | 50–150 | 0–30 |
| Cure Time (sec.) | 100–160 | 90–150 |
| Properties: | | |
| Specific Gravity | 1.57–1.62 | 1.57–1.62 |
| Linear Shrinkage (ADA Spec. 19) | 0.2–0.3% | 0.2–0.3% |
| Shore A Hardness | | |
| 10 min. | 60–70 | 60–70 |
| 20 min. | 70–80 | 65–75 |
| 60 min. | 75–85 | 70–80 |
| % Elongation | 50 | 59 |
| Tear Die (lb./in.) | 61 | 59 |
| Color | Gray | Gray |

The foregoing properties indicate that extremely useful dental impression compositions have been provided.

The base compounds of Examples 1 and 2 exhibit good shelf aging properties for 6 months or more, based on accelerated aging at 50° C.

Neither Mixtures A nor B (Examples 1 and 2) display any cure inhibition when used with custom trays made of polyvinylchloride, polyethylene, methyl methacrylate or epoxy materials.

The two examples given above represent compounds made of relatively high and low viscosity polyorganosiloxanes within the range of viscosities possible with the present compositions. Other blends, of course, are possible, such as blends of Mixtures A and B to achieve properties between the two.

EXAMPLE 3

This example is illustrative of the preparation and properties of a composition of the second embodiment, which is non-tacky and produces a very smooth cured vulcanizate. All proportions are on a percent by weight basis.

The base compound consists of a mixture of 17 parts of silanol stopped polydimethylsiloxane having a viscosity in the range of 20,000 to 30,000 cps. at 25° C., 5.2 parts of mineral oil (Wittco Chemical's Kaydol), 77 parts of low oil absorption calcium carbonate filler (Camel Kote), and 0.8 parts of 40% condensed ethyl orthosilicate. The Camel Kote filler has an estimated oil absorption value of about 10 lbs. oil/100 lbs. calcium carbonate, ASTM D-281-31. The base compound, before catalyzation, has a putty-like consistency and exhibits good handling characteristics, being non-tacky and non-gritty to the touch. This compound has a specific gravity of 1.85–1.90.

To initiate curing, stannous octoate catalyst is added and worked into the base compound in the ratio of 0.5 parts of catalyst per 100 parts of base compound. The resulting catalyzed dental impression composition has a work life of about 55 seconds at room temperature. After about 55 seconds have elapsed, the composition becomes difficult to handle or manipulate.

EXAMPLE 4

This example compares physical properties of room-temperature vulcanizable dental impression compositions according to the present invention, using various low oil absorption calcium carbonates as the filler in the base compound.

Base compounds are prepared according to the procedure of Example 3 using a different calcium carbonate filler in each case. The calcium carbonates employed, together with their corresponding oil absorption values, are summarized in Table 3.

TABLE 3

CALCIUM CARBONATE FILLERS

| Filler | Oil Absorption lbs. oil/100 lbs. filler (ASTM D-281-31) |
| --- | --- |
| Camel Kote | 10 |
| Gamma Sperse 255 | 10–12 |
| No. 10 White | 7–9 |
| Wingdale White | 11–13 |
| Duramite | 5–6 |
| Micro White 75 | 10–12 |

The initial work life of the base compounds using each of the above fillers is measured after catalyzing a portion of each base compound according to the procedure of Example 3. The Shore A hardnesses of the catalyzed compounds are also measured at intervals of 5 and 10 minutes after catalyzation. These properties are summarized in Table 4.

To measure the stability of the various base compounds, the uncatalyzed portions of each of the compounds are shelf aged at 50° C. for given time intervals (shown in Table 4), then catalyzed as above, and the work life and Shore A harnesses are measured. These properties are also summarized in Table 4.

TABLE 4

COMPARISON OF BASE COMPOUNDS USING VARIOUS LOW OIL ABSORPTION CALCIUM CARBONATE FILLERS

| Filler | Work Life (secs.) | Shore A Hardness 5 min. | 10 min. |
| --- | --- | --- | --- |
| Camel Kote | | | |
| Initial | 55 | 66 | 63 |
| After 245 days aging | 55 | 76 | 73 |
| Gamma Sperse 255 | | | |
| Initial | 50 | 70 | 80 |
| After 233 days aging | 55 | 60 | 72 |
| No. 10 White | | | |
| Initial | 60 | 70 | 73 |
| After 217 days aging | 60 | 37 | 50 |
| Wingdale White | | | |
| Initial | 70 | 65 | 77 |
| After 217 days aging | 95 | 43 | 60 |
| Duramite | | | |
| Initial | 45 | 79 | 81 |
| After 233 days aging | 35 | 30 | 42 |
| Microwhite 75 | | | |
| Initial | 60 | 68 | 75 |
| After 217 days aging | 60 | 53 | 68 |

The compositions employing Gamma Sperse 255 or Duramite as the filler have a slightly gritty feel. The compositions which employ Wingdale White or Micro White 75 are smooth but exhibit slight tack. The composition containing No. 10 White exhibits a slight tack and has a slight gritty feel. The composition using Camel Kote filler provides good handling, i.e., non-tacky and non-gritty. It should be noted that these properties, i.e., tack and gritty, are somewhat dependent on the subjective judgment of the individual who is doing the handling.

Although, all the above calcium carbonate fillers display acceptable properties, including handling, Camel Kote calcium carbonate appears to give the best overall performance. This appears to be due in part to the particle size distribution of Camel Kote calcium carbonate, which is unique in that it contains substantially no particles above 30 microns in size and relatively few particles below 5 microns in size. Thus while the oil absorption values of Camel Kote and No. 10 White are about the same, Camel Kote displays better handling characteristics, apparently because of the differences in particle size distribution between these two calcium carbonates.

It is to be understood that conventional additives may also be added to the present dental impression compositions, e.g., low-toxicity pigments and flavors.

Other compositions will suggest themselves to those skilled in the art in view of the above-detailed descriptions. All such obvious variations are within the full intended scope of the invention, which is defined in the appended claims.

I claim:
1. A room temperature vulcanizing silicone dental impression composition which, before curing, consists essentially of from about 0.3 to about 0.7 parts by weight of a metallic salt of a monocarboxylic acid as a catalyst to about 100 parts of a base composition consisting essentially of:
   a. from about 25 to about 35% by weight of a fluid diorganopolysiloxane containing terminal silicon-bonded hydroxy groups and having a viscosity of from 2,000 to 250,000 cps. at 25° C.;
   b. from about 60 to about 75% by weight of a filler composition consisting essentially of an admixture of zinc oxide, calcium carbonate and pumice, said zinc oxide and calcium carbonate each being present in at least a sufficient amount to provide bulking and whitening and said pumice being present in at least a sufficient amount to provide putty-like consistency;

c. from about 0.05 to about 2% by weight of an organo-silicon cross-linker having the general formula:

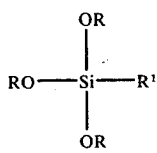

wherein R is a radical selected from the group consisting of alkyl, alkenyl and aryl radicals and $R^1$ is a member of the group consisting of alkyl, alkenyl, aryl and alkoxy radicals.

2. A composition as defined in claim 1 wherein the diorganopolysiloxane (a) is dimethylpolysiloxane.

3. A composition as defined in claim 2 wherein the viscosity of said dimethylpolysiloxane (a) is in the range from 80,000 to 120,000 cps. at 25° C., said composition having low flow and being non-tacky to the touch prior to catalyzing.

4. A composition as defined in claim 3 wherein the metallic salt catalyst is in the weight ratio of about 0.6 parts to 100 parts of the base composition.

5. A composition as defined in claim 3 wherein said diorganopolysiloxane includes a small but effective amount of a low molecular weight dimethyl polysiloxane containing terminal silicon-bonded hydroxy groups, to slow curing time.

6. A composition as defined in claim 5 wherein the low molecular weight dimethyl polysiloxane contains about 7% by weight of hydroxy groups and from 5 to 10 dimethyl siloxane units.

7. A composition as defined in claim 6 wherein the low molecular weight dimethyl polysiloxane is in the amount from about 0.05 to about 2% by weight of the base composition.

8. A composition as defined in claim 2 wherein the viscosity of the dimethylpolysiloxane is in the range from 2,500 to 3,500 cps. at 25° C., said composition having high flow and being tacky to the touch prior to catalyzing.

9. A composition as defined in claim 8 wherein the metallic salt catalyst is in the amount of about 0.4 parts by weight to 100 parts by weight of the base composition.

10. A composition as defined in claim 1 wherein the organo-silicon cross-linker (c) is condensed ethyl orthosilicate.

11. A composition as defined in claim 1 wherein the metallic salt catalyst is tin octoate.

12. A room temperature vulcanizing silicone dental impression compositon which, before curing, consists essentially of from about 0.3 to about 0.7 parts by weight of a metallic salt of a monocarboxylic acid as a catalyst to 100 parts of a base composition consisting essentially of:
a. from about 15 to about 25% by weight of a fluid diorganopolysiloxane containing terminal silicon-bonded hydroxy groups and having a viscosity of from about 15,000 to about 35,000 centipoise at 25° C.;
b. from about 70 to about 85% by weight of a filler consisting essentially of low oil absorption calcium carbonate;
c. from about 3 to about 8% by weight of mineral oil; and
d. from about 0.05 to about 2% by weight of an organo-silicon cross-linker having the general formula:

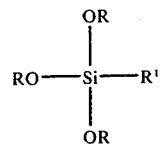

wherein R is a radical selected from the group consisting of alkyl, alkenyl and aryl radicals and $R^1$ is a member of the group consisting of alkyl, alkenyl, aryl and alkoxy groups, said composition having a non-sticky feel before curing, and a smooth, non-grainy appearance after curing.

13. A composition as defined in claim 12 wherein the diorganopolysiloxane (a) is a dimethylpolysiloxane.

14. A composition as defined in claim 13 wherein the viscosity of said dimethyl polysiloxane is in the range of from 15,000 to 35,000 cps. at 25° C.

15. A composition as defined in claim 12 wherein the organo-silicon cross-linker (d) is condensed ethyl orthosilicate.

16. A composition as defined in claim 12 wherein the metallic salt is tin octoate.

17. A room temperature vulcanizing silicone dental impression composition which, before curing, consists essentially of from about 0.3 to about 0.7 parts by weight of a metallic salt of a monocarboxylic acid as a catalyst to about 100 parts of a base composition consisting essentially of:
a. from about 25 to about 35% by weight of a fluid diorganopolysiloxane containing terminal silicon-bonded hydroxy groups and having a viscosity of from 2,000 to 250,000 cps. at 25° C.;
b. from about 60 to about 75% by weight of a filler composition consisting essentially of an admixture of 3 to 15 parts of zinc oxide, 5 to 25 parts of calcium carbonate and 45 to 65 parts of pumice, based on 100 parts by weight of the base composition;
c. from about 0.05 to about 2% by weight of an organo-silicon cross-linker having the general formula:

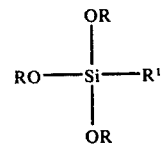

wherein R is a radical selected from the group consisting of alkyl, alkenyl and aryl radicals and $R^1$ is a member of the group consisting of alkyl, alkenyl, aryl and alkoxy radicals.

* * * * *